United States Patent
Shin et al.

(10) Patent No.: US 12,285,546 B2
(45) Date of Patent: Apr. 29, 2025

(54) ANIMAL FAT-DERIVED EXTRACELLULAR MATRIX, AND PRESERVATION SOLUTION OF ANIMAL FAT-DERIVED EXTRACELLULAR MATRIX

(71) Applicant: DOF INC., Hwaseong-si (KR)

(72) Inventors: Yong-Woo Shin, Seongnam-si (KR); Seong-Rae No, Seongnam-si (KR); Min-Cheol Kook, Seongnam-si (KR); Kyu-Byung Kim, Gwangju-si (KR); Yoon-Hee Seol, Seongnam-si (KR); Jee-Hoon Shin, Seongnam-si (KR)

(73) Assignee: DOF INC., Daejeon (KR)

( * ) Notice: Subject to any disclaimer, the term of this patent is extended or adjusted under 35 U.S.C. 154(b) by 852 days.

(21) Appl. No.: 17/594,602

(22) PCT Filed: Nov. 21, 2019

(86) PCT No.: PCT/KR2019/016067
§ 371 (c)(1),
(2) Date: Oct. 22, 2021

(87) PCT Pub. No.: WO2021/040141
PCT Pub. Date: Mar. 4, 2021

(65) Prior Publication Data
US 2022/0202995 A1    Jun. 30, 2022

(30) Foreign Application Priority Data
Aug. 27, 2019 (KR) .................. 10-2019-0105041

(51) Int. Cl.
*A61L 27/54* (2006.01)
*A61L 27/36* (2006.01)

(52) U.S. Cl.
CPC .............. *A61L 27/54* (2013.01); *A61L 27/36* (2013.01)

(58) Field of Classification Search
None
See application file for complete search history.

(56) References Cited

U.S. PATENT DOCUMENTS

| | | |
|---|---|---|
| 10,537,663 B2 | 1/2020 | Jung et al. |
| 2012/0189588 A1 | 7/2012 | Nahas et al. |
| 2014/0271784 A1 | 9/2014 | Yang et al. |
| 2016/0051722 A1 | 2/2016 | Lee et al. |

FOREIGN PATENT DOCUMENTS

| | | | | |
|---|---|---|---|---|
| CN | 102575229 A | * | 7/2012 | ............. A61K 35/12 |
| JP | 6-304242 A | | 11/1994 | |
| JP | 2007-105081 A | | 4/2007 | |
| KR | 10-2009-0131432 A | | 12/2009 | |
| KR | 10-2014-0084265 A | | 7/2014 | |
| KR | 10-1772316 B | | 8/2017 | |
| WO | 2009/154344 A1 | | 12/2009 | |
| WO | WO 2011019822 A2 | | 2/2011 | |
| WO | 2013/063580 A1 | | 5/2013 | |
| WO | 2017/155328 A1 | | 9/2017 | |

OTHER PUBLICATIONS

Wang et al., "Supercritical carbon dioxide extracted extracellular matrix material from adipose tissue". Materials & Science Engineering: C. vol. 75, 2017. (Year: 2017).*
Luo et al., "From Flab to Fab: Transforming Surgical Waste into an Effective Bioactive Coating Material". Advanced Healthcare Materials. 2015. (Year: 2015).*
Chinese Office Action, mailed Jun. 28, 2022, for Chinese Application No. 2019800997213, 11 pages. (with English Translation).
Wang et al., "Supercritical carbon dioxide extracted extracellular matrix material from adipose tissue," *Materials Science and Engineering* C75:349-358, Feb. 2, 2017.
Office Action (w/ English Translation), mailed Jan. 20, 2023, for Chinese Application No. 2019800997213. (10 pages).
International Search Report and Written Opinion, dated May 25, 2020, for International Application No. PCT/KR2019/016067. (w/ English Translation of International Search Report) (9 pages).

* cited by examiner

*Primary Examiner* — Robert M Kelly
*Assistant Examiner* — John David Moore
(74) *Attorney, Agent, or Firm* — Seed IP Law Group LLP

(57) ABSTRACT

The present invention provides: an extracellular matrix of which the biocompatibility is greatly increased through fat removal and decellularization and which contains growth factors so as to control physiological activities of cells; and a method for preparing the same. In addition, the extracellular matrix may be effectively obtained through a solvent extraction process using supercritical fluid, and a preservation solution comprising the extracellular matrix may be preserved for a long time by preventing contamination, and has increased manageability so that usability of the extracellular matrix may be greatly increased.

5 Claims, 12 Drawing Sheets

Adipose tissue     Adipose tissue after supercritical extraction

Adipose tissue

Adipose tissue after supercritical extraction

Supercritical Extraction Sample     1 wt% dispersion     Filtering Solution

Before filtration        After filtration

ANIMAL FAT-DERIVED EXTRACELLULAR MATRIX, AND PRESERVATION SOLUTION OF ANIMAL FAT-DERIVED EXTRACELLULAR MATRIX

TECHNICAL FIELD

The present invention relates to an animal fat-derived extracellular matrix and a preservation solution of an animal fat-derived extracellular matrix, and more particularly, to an animal fat-derived extracellular matrix with very excellent biocompatibility and physiological functions.

BACKGROUND

An extracellular matrix is a tissue mainly responsible for the structural support of animals. As a simple intercellular linkage, it can play very importants role as a structural factor as well as a regulator of cell physiology such as cell division, differentiation, and death.

The extracellular matrix is composed of connective tissue fibers, amorphous components, and extracellular fluid.

The connective tissue fibers are formed in a triple helix structure, and are mainly composed of collagen and elastin, which provide strength and elasticity to the extracellular matrix.

The amorphous component is mainly composed of glycosaminoglycans (GAGs) and proteoglycan combined with a protein (core protein). Due to the negative charge, it combines with a large amount of water to form a gel in the extracellular matrix.

These connective tissue fibers and amorphous components help a buffer action of the extracellular matrix.

The extracellular fluid contains ions, fat, glucose, amino acids, and the like, so that cells can survive and perform specific functions, and physiological factors such as protease and growth factors exist.

A growth factor is a generic term for polypeptides that promote division or growth differentiation of various cells.

Several types of growth factors have been found, and growth factors have various functions, and are known to be involved in the cell signaling system.

In addition to the nutrients that constitute the basic components of organisms, they are necessary for cell proliferation and the growth and development of living organisms and essential for cell growth and differentiation.

If we can store and properly supply them and provide a physical environment in which cells can recognize them, the survival, growth, migration, differentiation, and the like of cells can be greatly promoted.

Using the properties of the extracellular matrix, recently, extracellular matrix-derived biosupport materials have been widely used in tissue engineering and regenerative medicine.

In particular, various biomaterials such as tissue repair material and dressing bands using the extracellular matrix have been introduced, but currently commercialized products use only some components of the extracellular matrix.

Although various chemical and biological methods have been developed to extract the extracellular matrix, the extracellular matrix that does not lose the growth factors, which is the most important for the physiological activity of cells, during the extraction process from animal adipose tissue has not been disclosed yet.

The related prior literature includes Korean Patent No. 10-1772316 (published on Aug. 29, 2017), which discloses a method for preparing a biocompatible porcine cartilage-derived extracellular matrix membrane capable of controlling in vivo degradation rate and physical properties, and an anti-adhesion composition containing the porcine cartilage-derived extracellular matrix as an active ingredient.

DETAILED DESCRIPTION OF INVENTION

Technical Problem

Therefore, the present invention provides an extracellular matrix of which the biosafety and biocompatibility are increased through decellularization and fat removal while effectively extracting the extracellular matrix from animal fat and which contains a large amount of growth factors capable of regulating physiological activities of cells; and a method for preparing the same.

The problem to be solved by the present invention is not limited to the problem(s) mentioned above, and another problem(s) not mentioned will be clearly understood by one of ordinary skill in the art from the following description.

Solution to Problem

In order to solve the above problems, according to an aspect of the present invention, the present invention provides an animal fat-derived extracellular matrix, which has undergone decellularization and fat removal and contains certain growth factors.

In addition, the decellularization and fat removal and the inclusion of growth factors may be carried out through a solvent extraction process using supercritical fluid.

In addition, the solvent extraction process using supercritical fluid may remove lipids remaining in the animal fat and sterilize to increase biocompatibility.

In addition, the animal fat may be waste adipose tissue extracted through liposuction.

In addition, the growth factor may consist of AR, bFGF, b-NGF, EGF, EGFR, FGF-6, FGF-7, GCSF, GDNF, GM-CSF, HB-EGF, HGF, IGFB P-1, IGFB P-2, IGFB P-3, IGFB P-4, IGFB P-6, IGF-I, IGF-ISR, IGF-II, M-CSF, M-CSFR, NT-3, NT-4, PDGFRa, PDGFRb, PDGF-AA, PDGF-AB, PDGF-BB, PIGF, SCF, SCFR, TGF-a, TGF-b, TGF-b2, TGF-b3, VEGF, VEGFR2, VEGFR3, and VEGF-D.

In addition, the growth factor may be contained in an amount of 0.52 to 11.19 ng per 1 g of the extracellular matrix.

According to another aspect of the present invention, the present invention provides an animal fat-derived extracellular matrix preservation solution, wherein it contains 0.1 to 5 parts by weight of an animal fat-derived extracellular matrix that has undergone decellularization and fat removal through a solvent extraction process using supercritical fluid and contains certain growth factors; and 95 to 99.9 parts by weight of a dispersion, and is filtered.

In addition, the growth factor may consist of AR, bFGF, b-NGF, EGF, EGFR, FGF-6, FGF-7, GCSF, GDNF, GM-CSF, HB-EGF, HGF, IGFB P-1, IGFB P-2, IGFB P-3, IGFB P-4, IGFB P-6, IGF-I, IGF-ISR, IGF-II, M-CSF, M-CSFR, NT-3, NT-4, PDGFRa, PDGFRb, PDGF-AA, PDGF-AB, PDGF-BB, PIGF, SCF, SCFR, TGF-a, TGF-b, TGF-b2, TGF-b3, VEGF, VEGFR2, VEGFR3, and VEGF-D, and may be filtered and contained in an amount of 0.21 to 6.86 ng per 1 g of the extracellular matrix.

In addition, the growth factor may have the reduced content of bFGF (basic fibroblast growth factor) in the range of 40 to 50% through the filtration.

Effects of Invention

According to the present invention, there is provided an extracellular matrix of which the biocompatibility is greatly increased through fat removal and decellularization and which contains growth factors so as to control physiological activities of cells, and a method for preparing the same.

In addition, the extracellular matrix may be effectively obtained through a solvent extraction process using supercritical fluid.

In addition, it may be sterilized without acid, enzyme treatment and radiation treatment to increase the biosafety of the extracellular matrix, and may undergo decellularization and fat removal to increase biocompatibility.

In addition, it provides an extracellular matrix in which growth factors are preserved among the components of the extracellular matrix, and the regulation of physiological activities of cells may be expected by controlling the content of growth factors, and the regeneration of tissues may be quickly induced.

In addition, it is possible to maintain the structural properties of the extracellular matrix as it is, so that it is possible to readily prepare a tissue structure mimic that may be molded according to the shape of the transplant site.

In addition, the extracellular matrix may be effectively extracted and provided by effectively treating human-derived waste fat.

In addition, a preservation solution containing the extracellular matrix may be preserved for a long time by preventing contamination, and has increased manageability so that usability of the extracellular matrix may be greatly increased.

The effect of the present invention is not limited to the above effects, and it should be understood to include all effects that may be inferred from the configuration of the invention described in the detailed description or claims of the present invention.

MODE FOR CARRYING OUT THE INVENTION

Figure 1:
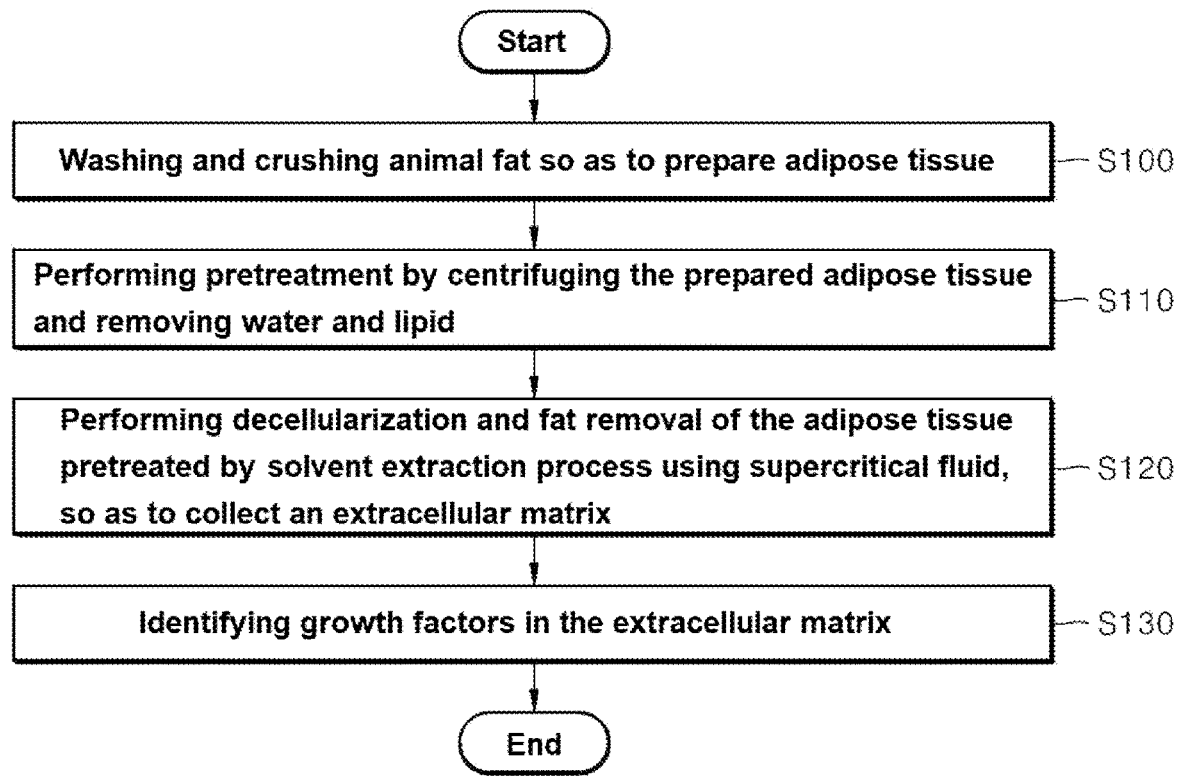
FIG. 1 is a process flow diagram of a method for preparing an animal fat-derived extracellular matrix according to an embodiment of the present invention.

Hereinafter, preferred embodiments according to the present invention will be described in detail with reference to the accompanying drawings.

Advantages and features of the present invention and a method of achieving the same will become apparent with reference to the embodiments described below in detail in conjunction with the accompanying drawings.

However, the present invention is not limited by the embodiments disclosed below, but will be implemented in various different forms, and these embodiments only allow the disclosure of the present invention to be complete, and are provided to fully inform one of ordinary skill in the art to which the present invention belongs the scope of the invention, and the present invention is only defined by the scope of the claims.

In addition, in the description of the present invention, when it is determined that related known techniques may obscure the gist of the present invention, a detailed description thereof will be omitted.

The present inventors found that conventional methods for extracting extracellular matrix (ECM) from animal fat are not suitable for effectively obtaining extracellular matrix. The reason is that the conventional methods mainly extract and treat the extracellular matrix through radiation irradiation along with chemical treatment and biological treatment to increase biosafety, biocompatibility, physical properties such as mechanical properties, but there is a problem that the growth factor contained in the extracellular matrix may be easily destructed by chemical treatment, biological treatment, and radiation treatment, and the process uses a large amount of acids and enzymes and uses radiation, and thus, the risk of controlling the process is high, and the efficiency is greatly reduced.

On the other hand, a solvent extraction process using supercritical fluid may effectively extract the extracts without physical change thereof through the solvent in the supercritical state, and thus, may maintain the mechanical performance properties of the extracts. In particular, when a supercritical fluid solvent extraction is applied to animal fat under certain conditions, the extracellular matrix may be effectively obtained, of which the biostability and biocompatibility are greatly increased through decellularization and fat removal, and in which the content of growth factors, which are unique components of the extracellular matrix, is controlled so as to regulate physiological activities of cells. Based on the above, the present inventors completed the present invention.

Hereinafter, the present invention will be described in detail.

An animal fat-derived extracellular matrix according to the present invention has undergone decellularization and fat removal and contains certain growth factors.

The animal fat may be porcine fat, and preferably waste fat extracted through liposuction.

Recently, a lot of liposuctions for cosmetic surgery has been performed, so a large amount of human-derived fat may be obtained. However, when extracting useful substances of stem cells and extracellular matrix in such liposuction, it is difficult to utilize the extracted human fat because unnecessary components such as blood and lipids are contained. Therefore, when increasing the biostability and biocompatibility by decellularization and fat removal through a solvent extraction process using supercritical fluid, it may be safely and effectively transplanted into the human body.

The animal fat is not limited as long as it contains an extracellular matrix in the tissue.

The decellularization and fat removal may be carried out through a solvent extraction process using supercritical fluid.

In the solvent extraction process using supercritical fluid, the pressure during the preparation of the supercritical fluid solvent, and the flow rate, the reaction process temperature, and time introduced into the animal adipose tissue to be extracted are controlled, so that the animal adipose tissue may undergo decellularization and fat removal.

The solvent extraction process using supercritical fluid may remove the blood remaining in the animal fat and sterilize it to increase biocompatibility.

The solvent extraction process using supercritical fluid may increase the solubility of the supercritical fluid in animal fat by adding ethanol as a co-solvent, and may effectively remove blood and contaminants remaining in the animal fat to sterilize.

The solvent extraction process using supercritical fluid extracts the extracellular matrix from the animal fat, and it is possible to allow the extracellular matrix to contain certain growth factors.

When the extracellular matrix contains growth factors, it is possible to control physiological activities of cells, and when it is injected into human tissue in the form of a tissue repair material, tissue regeneration may be rapidly induced.

The growth factor consists of AR, bFGF, b-NGF, EGF, EGFR, FGF-6, FGF-7, GCSF, GDNF, GM-CSF, HB-EGF, HGF, IGFB P-1, IGFB P-2, IGFB P-3, IGFB P-4, IGFB P-6, IGF-I, IGF-ISR, IGF-II, M-CSF, M-CSFR, NT-3, NT-4, PDGFRa, PDGFRb, PDGF-AA, PDGF-AB, PDGF-BB, PIGF, SCF, SCFR, TGF-a, TGF-b, TGF-b2, TGF-b3, VEGF, VEGFR2, VEGFR3, and VEGF-D.

The extracellular matrix contains 40 types of growth factors except for fibroblast growth factor-4 (FGF-4) among human growth factors through a solvent extraction process using supercritical fluid.

The FGF-4 is removed in the process of decellularization and fat removal of animal fat through a solvent extraction process using supercritical fluid, and an extracellular matrix according to an embodiment of the present invention is characterized in that the FGF-4 growth factor is excluded.

The growth factor may be contained in an amount of 0.52 to 11.19 ng per 1 g of the extracellular matrix.

The extracellular matrix obtained through the solvent extraction process using supercritical fluid contains growth factors in a certain amount or more even after decellularization and fat removal, so that biocompatibility may be greatly increased, the physiological activity of cells may be controlled, and tissue regeneration may be rapidly induced.

When the animal fat is collected through acid and enzyme treatment, and radiation treatment instead of the solvent extraction process using supercritical fluid, it is difficult to collect all of the 40 types of growth factors. In particular, the enzyme treatment method easily degrades a growth factor, which is a peptide, and thus, it is not possible to obtain an extracellular matrix having an effective content within the above range.

According to another aspect of the present invention, the present invention provides an animal fat-derived extracellular matrix preservation solution, wherein it comprises 0.1 to 5 parts by weight of an animal fat-derived extracellular matrix that has undergone decellularization and fat removal through a solvent extraction process using supercritical fluid and contains certain growth factors; and 95 to 99.9 parts by weight of a dispersion, and is filtered.

The extracellular matrix collected by a solvent extraction process using supercritical fluid may maintain mechanical properties, but it is not easy to manufacture various applications in a solid state.

When the extracellular matrix obtained through the solvent extraction process using supercritical fluid is dispersed in a dispersion and filtered, biosafety and biocompatibility are increased by removing high molecular weight proteins, and 0.1 to 5 wt % or less of the extracellular matrix is dispersed in a dispersion to increase the manageability and to greatly increase the usability.

If the extracellular matrix collected by a solvent extraction process using supercritical fluid is contained within the above range, it may be preserved for a long time without changing the content of growth factors in the extracellular matrix.

The growth factor consists of AR, bFGF, b-NGF, EGF, EGFR, FGF-6, FGF-7, GCSF, GDNF, GM-CSF, HB-EGF, HGF, IGFB P-1, IGFB P-2, IGFB P-3, IGFB P-4, IGFB P-6, IGF-I, IGF-ISR, IGF-II, M-CSF, M-CSFR, NT-3, NT-4, PDGFRa, PDGFRb, PDGF-AA, PDGF-AB, PDGF-BB, PIGF, SCF, SCFR, TGF-a, TGF-b, TGF-b2, TGF-b3, VEGF, VEGFR2, VEGFR3, and VEGF-D.

The animal fat-derived extracellular matrix preservation solution contains 40 types of growth factors except for fibroblast growth factor-4 (FGF-4) among human growth factors.

The growth factor may be filtered and contained in an amount of 0.21 to 6.86 ng per 1 g of the extracellular matrix.

The animal fat-derived extracellular matrix preservation solution is filtered to control the content of growth factors.

The filtration may prevent contamination of the preservation solution by removing proteins in the extracellular matrix, and may allow for growth factors to be contained within the above range.

The animal fat-derived extracellular matrix preservation solution may have the reduced content of growth factor within the above range relative to an animal fat-derived extracellular matrix content, but it may effectively preserve the extracellular matrix and greatly increases its usability.

The dispersion may be deionized water.

When deionized water is selected as the dispersion, it is possible to prevent contamination when dispersing the extracellular matrix, thereby increasing preservation.

The filtration may be performed using a filter having a pore size of 0.2 to 0.45 μm.

By using a filter within the above range, it is possible to effectively reduce the risk of contamination by removing high molecular weight proteins remaining in the extracellular matrix, to sterilize the preservation solution, and to effectively remove the remaining DNA.

If it is out of the above range, there is a concern that growth factors are reduced in the preservation solution, or the extracellular matrix in addition to proteins is removed together, and there is a risk of infection and DNA remaining, thereby reducing biocompatibility.

The growth factor may have the reduced content of bFGF (basic fibroblast growth factor) in the range of 40 to 50% through the filtration.

The bFGF is contained in or bound to the protein, and when the protein is removed by filtration in the preservation solution through the filtration, the bFGF is filtered together and thus the content thereof is reduced.

According to another aspect of the present invention, the present invention provides a method for preparing an animal fat-derived extracellular matrix.

FIG. 1 is a process flow diagram of a method for preparing an animal fat-derived extracellular matrix according to an embodiment of the present invention.

Referring to FIG. 1, a method for preparing an animal fat-derived extracellular matrix comprises the following steps:
(1) washing and crushing animal fat so as to prepare adipose tissue;
(2) performing pretreatment by centrifuging the prepared adipose tissue and removing water and lipid;
(3) performing decellularization and fat removal of the adipose tissue pretreated by solvent extraction process using supercritical fluid, so as to collect an extracellular matrix; and
(4) identifying growth factors in the extracellular matrix.

First, wash and crush animal fat so as to prepare adipose tissue (S100).

The animal fat may be porcine fat, and preferably waste fat extracted through liposuction.

When the animal fat is waste tissue derived from the human body, it is possible to remove contaminants such as the remaining blood through washing, and if crushing is performed, the efficiency of centrifugation may be increased in a subsequent step.

Pretreatment is performed by centrifuging the prepared adipose tissue and removing water and lipid (S110).

Through the centrifugation, animal fat may be separated into water in the lower layer and lipid in the upper layer. In case of solvent extraction of the solid content in the middle layer from which the water in the lower layer and the lipid in the upper layer have been removed, the efficiency of the subsequent solvent extraction process using supercritical fluid may be greatly increased.

Decellularization and fat removal of the pretreated adipose tissue is performed by using a solvent extraction process using supercritical fluid, so as to collect an extracellular matrix (S120).

In the solvent extraction process using supercritical fluid, the solvent extraction conditions may be changed for decellularization and fat removal of the adipose tissue.

In an embodiment of the present invention, in the solvent extraction process using supercritical fluid, a supercritical fluid may be prepared by pressurizing carbon dioxide to 200 to 600 bar, and the supercritical fluid may be infiltrated into the animal fat at a flow rate of 18 to 70 mL/min, at 30° C. to 35° C. for 2 to 12 hours, and the extracellular matrix may be extracted.

The supercritical fluid produced by pressurization within the above range may infiltrate the cell membrane of adipose tissue and dissolve intracellular lipids to defat it, and when the prepared supercritical fluid infiltrates into adipose tissue at a flow rate within the above range, decellularization and fat removal may be performed while maintaining the mechanical properties of the extracellular matrix.

In the solvent extraction process using supercritical fluid, the contaminants remaining in the adipose tissue are removed once more, thereby increasing the contamination prevention and sterilization effect.

Growth factors is identified in the extracellular matrix (S130).

The decellularized and defatted extracellular matrix may be effectively obtained through the solvent extraction process using supercritical fluid, and growth factors present in the extracellular fluid among the extracellular matrix may be also retained in a large amount.

Through a process of identifying the growth factor, it is possible to obtain an extracellular matrix containing a large amount of growth factors that may control physiological activities of cells and rapidly induce tissue regeneration.

In order to identify the growth factor, the level of any one growth factor selected from the group consisting of VEGF, bFGF, IGF-1 and EGF among growth factors may be analyzed by enzyme-linked immunosorbent assay to identify the content of the growth factors.

The enzyme-linked immunosorbent assay is very preferable because it is possible to identify the content of the growth factors contained in the extracellular matrix based on any one growth factor selected from the group consisting of VEGF, bFGF, IGF-1 and EGF. However, as long as it is a method capable of identifying the content of the growth factors, it is not particularly limited.

On the other hand, according to another aspect of the present invention, the present invention provides a method for preparing an animal fat-derived extracellular matrix preservation solution.

Figure 2:
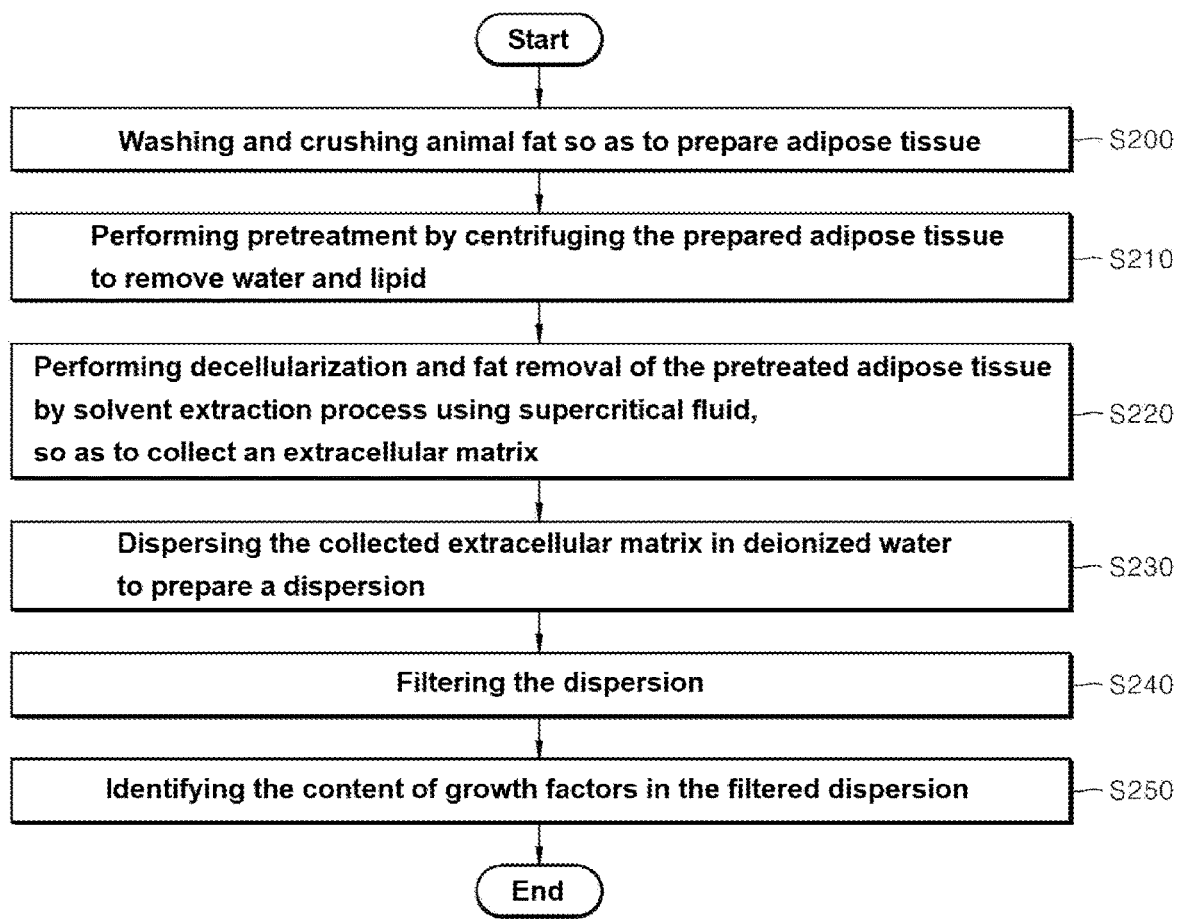
FIG. 2 is a process flow diagram of an animal fat-derived extracellular matrix preservation solution according to another embodiment of the present invention.

FIG. 2 is a process flow diagram of an animal fat-derived extracellular matrix preservation solution according to another embodiment of the present invention.

Referring to FIG. 2, a method for preparing an animal fat-derived extracellular matrix preservation solution comprises the following steps:
(a) washing and crushing animal fat so as to prepare adipose tissue;
(b) performing pretreatment by centrifuging the prepared adipose tissue to remove water and lipid;
(c) performing decellularization and fat removal of the pretreated adipose tissue by solvent extraction process using supercritical fluid, so as to collect an extracellular matrix;
(d) dispersing the collected extracellular matrix in deionized water to prepare a dispersion;
(e) filtering the dispersion; and
(f) identifying the content of growth factors in the filtered dispersion.

First, animal adipose tissue is washed and crushed so as to prepare adipose tissue (S200).

Pretreatment is performed by centrifuging the prepared adipose tissue and removing water and lipid (S210).

Decellularization and fat removal of the pretreated adipose tissue is performed by using a solvent extraction process using supercritical fluid, so as to collect an extracellular matrix (S220).

Since the steps S200 to S220 are the same process as in the method for preparing an animal fat-derived extracellular matrix, repeated descriptions below will be omitted.

The collected extracellular matrix is dispersed in deionized water to prepare a dispersion (S230).

When the dispersion is prepared by dispersing it in the deionized water, subsequent filtration is easy, and the content of the growth factor may be readily identified to prepare an extracellular matrix preservation solution.

The dispersion may be dispersed at a pressure of 15,000 to 25,000 psi at 15° C. using a high-pressure homogenizer.

When dispersed within the above range, the mechanical properties of the extracellular matrix may be maintained, and the proteins remaining in the extracellular matrix may be eluted and dispersed into the dispersion.

At this time, dispersion may be repeated 1 to 5 times depending on the suspension state.

The dispersion is filtered (S240).

Since the dispersion is a suspension in which the protein of the extracellular matrix remains, there is a risk of contamination and infection.

By removing the protein remaining through the filtration, it is possible to prevent contamination and infection of the extracellular matrix preservation solution to increase the biosafety, and it is also possible to increase the manageability and usability.

The filtration may be performed by passing the dispersion through a syringe filter having a pore size of 0.2 to 0.45 μm.

By using a filter having a pore size within the above range, it is possible to effectively remove the protein remaining together with the extracellular matrix, to maintain the preservation solution in a sterilized state, and to effectively remove the remaining DNA.

If it is out of the above range, the content of the extracellular matrix is reduced, so growth factors are reduced or it may not be sterilized due to the risk of infection, and it is difficult to remove the remaining DNA.

The content of growth factors is identified in the filtered dispersion (S250).

The growth factor may have the reduced content of bFGF (basic fibroblast growth factor) in the range of 40 to 50% through the filtration.

The bFGF is contained in or bound to the protein, and when the protein is removed by filtration in the preservation solution through the filtration, the bFGF is filtered together and thus the content thereof is reduced. Therefore, by identifying the decrease in the content of the bFGF, it may be identified whether the protein in the preservation solution is removed, and an animal fat-derived extracellular matrix preservation solution with increased biosafety may be prepared.

Hereinafter, preferred examples are presented to help the understanding of the present invention, but the following examples are only illustrative of the present invention and the scope of the present invention is not limited to the following examples.

EXAMPLE 1

Extracellular Matrix Extracted by Supercritical Fluid

In order to obtain an extracellular matrix from animal fat through a solvent extraction process using supercritical fluid, the waste fat obtained during liposuction was treated to prevent contamination and transferred, and then using a separatory funnel, enough deionized water was injected to the extent that the blood contained in fat was completely washed away to the naked eye, mixed, and then left for 20 minutes and washed. Washing were performed a total of 5 times.

1000 mL of the washed fat was put in a flask, dispersed at 50 rpm using a stirrer, and then passed through the ultrasonicator at a constant flow rate using a pump (pumping at 120 rpm), so that the ultrasonic wave may be uniformly transmitted through the entire fat.

The output of the ultrasonic wave was controlled to 70% amplitude at 400 W, and the fat was crushed for 6 minutes to obtain adipose tissue.

Adipose tissue was maintained at 3° C. using a chiller during ultrasonic treatment.

The ultrasonic treated adipose tissue was transferred to a centrifuge and centrifuged at 4,000 rpm for 20 minutes, and the water in the lower layer and the lipid in the upper layer were separated and removed.

The solid content in the middle layer was collected and placed in the reactor.

The reactor was equipped with a carbon dioxide cylinder on one side, and a cooler and a pump were provided along a line for discharging carbon dioxide to pressurize carbon dioxide to prepare a solvent as a supercritical fluid.

A tank for ethanol, a co-solvent, was provided on one side of the carbon dioxide cylinder, and a pump was provided on the line through which the ethanol is discharged. The ethanol was added to the solvent as the supercritical fluid to increase the solubility of the solvent, and the contaminants remaining in the adipose tissue were sterilized so as to show a sterilization effect.

It is performed the solvent extracting by introducing a solvent pressurized to 300 bar into the reactor and mixed with ethanol as a co-solvent at 32° C. at a flow rate of 20 mL/min.

The extraction time was carried out from 2 hours to 12 hours, and after the extraction was completed, the vent of the trap chamber equipped in the reactor was opened and the solvent was removed by evaporation to obtain the extracellular matrix as a white solid.

EXPERIMENTAL EXAMPLE 1

Physical Property of Extracellular Matrix

Protein quantitative analysis (Bicinchonic Acid Assay; BCA) was performed to identify the protein content in the extracellular matrix obtained by a solvent extraction process using supercritical fluid.

According to the protein quantitative analysis method, a total amount of the injected protein was adjusted to 70 μg, and then electrophoresis was performed.

Figure 3:
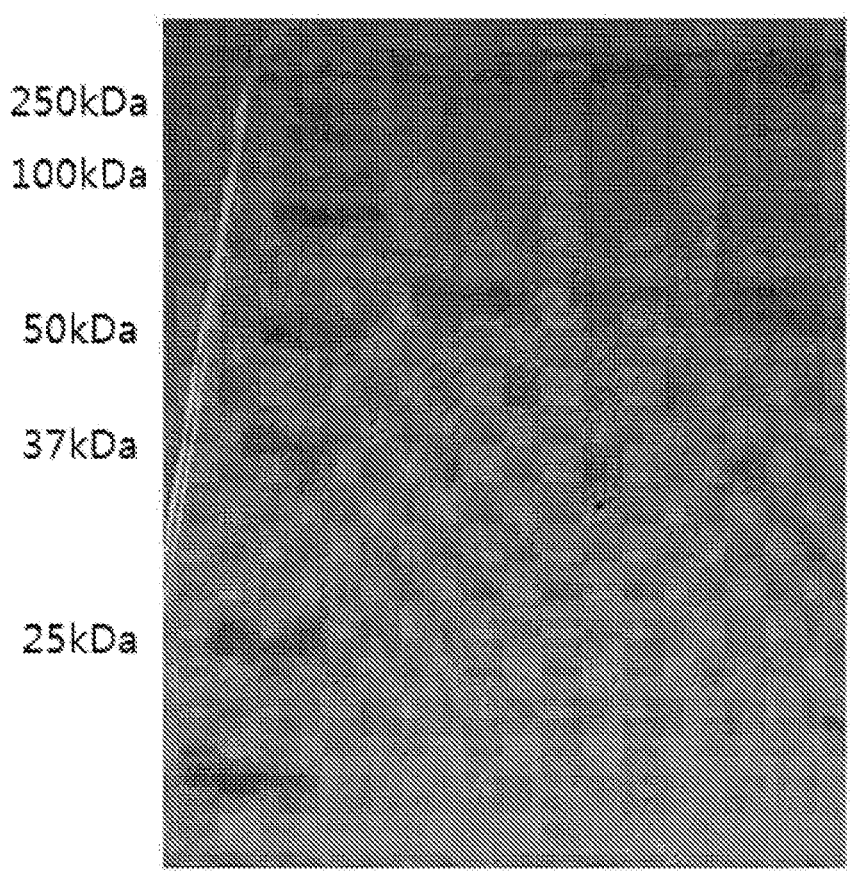
FIG. 3 is an electrophoresis photograph according to quantitative analysis of protein of an animal fat-derived extracellular matrix according to an embodiment of the present invention.

FIG. 3 is an electrophoresis photograph according to quantitative analysis of protein of an animal fat-derived extracellular matrix according to an embodiment of the present invention.

Referring to FIG. 3, from the left, there were a marker, and two types of samples, a fat sample before extraction, and a sample after extraction. The bands were maintained without change even after extraction.

Since the bands were maintained when the same amount of protein was injected, it was identified that it was defatted after supercritical extraction, and the protein was maintained without change.

Figure 4:
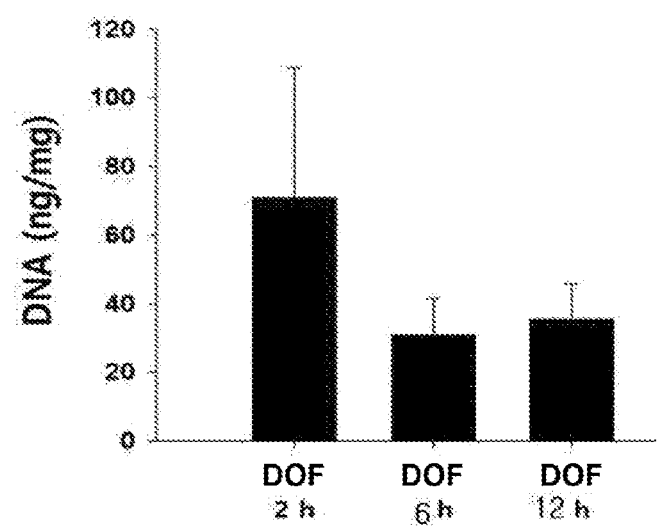
FIG. 4 is a graph showing the residual amount of DNA in an animal fat-derived extracellular matrix according to an embodiment of the present invention.

FIG. 4 is a graph showing the residual amount of DNA in an animal fat-derived extracellular matrix according to an embodiment of the present invention.

TABLE 1

| Extraction time | DNA content (ng/mg) |
|---|---|
| 2 hours | 70.72211 |
| 6 hours | 31.07875 |
| 12 hours | 35.60731294 |

Table 1 above shows the content of DNA remaining in the extracellular matrix according to the solvent extraction time in solvent extraction using a supercritical solvent of animal fat. Referring to FIG. 4 and Table 1, it was identified that when supercritical extraction was performed for 2 hours, the content of DNA was about 70 ng/mg, whereas when supercritical extraction was performed for 12 hours, the residual amount of DNA was about 35 ng/mg. Therefore, it was identified that the DNA content that may cause an immune response may be effectively reduced, and that the nucleus in the cell is destructed and decellularized.

On the other hand, Hematoxylin and Eosin staining was performed to identify that the extracellular matrix obtained by a solvent extraction process using supercritical fluid was decellularized.

Figure 5:
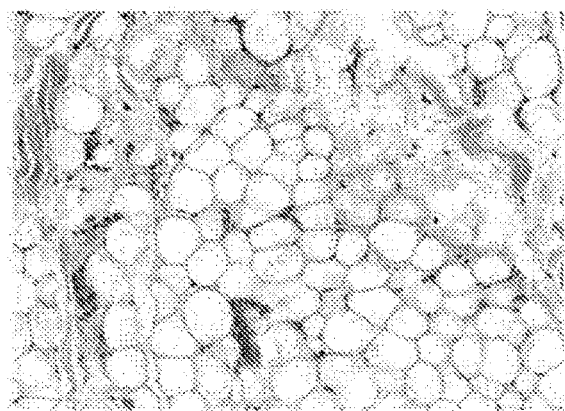
FIG. 5 is photographs of Hematoxylin and Eosin staining of an animal fat-derived extracellular matrix according to an embodiment of the present invention.
Figure 5:
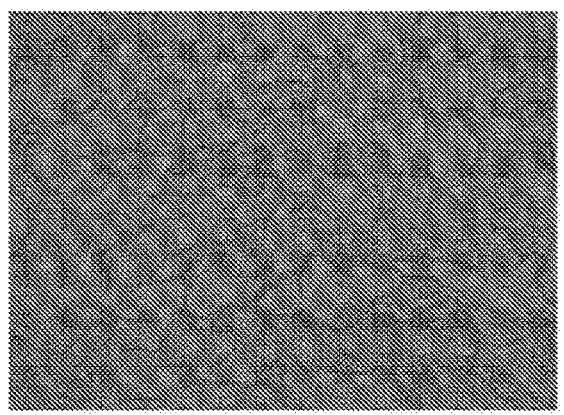

FIG. 5 is photographs of Hematoxylin and Eosin staining of an animal fat-derived extracellular matrix according to an embodiment of the present invention.

Referring to FIG. 5, in order to compare the effect of a solvent extraction process using supercritical fluid, the staining photograph of adipose tissue before supercritical extraction is shown on the left, and the staining photograph of the extracellular matrix obtained after a solvent extraction process using supercritical fluid is shown on the right.

After a solvent extraction process using supercritical fluid, cell nuclei could not be observed in the extracellular matrix, and it was identified that the cells were decellularized by identifying that the cells did not maintain their shape.

Figure 6:
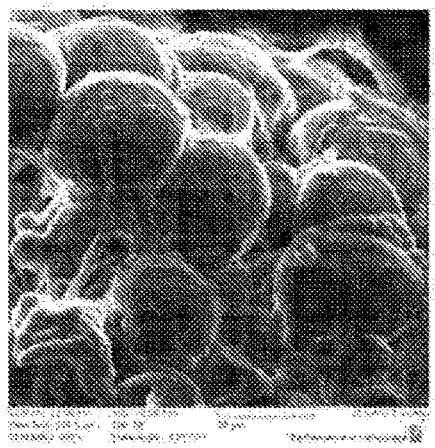
FIG. 6 is scanning electron microphotographs of an animal fat-derived extracellular matrix according to an embodiment of the present invention.
Figure 6:
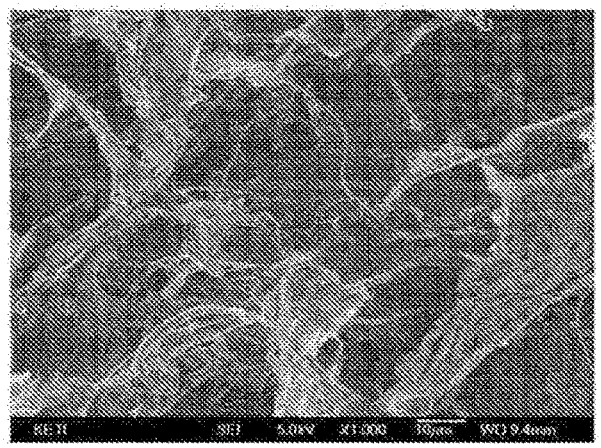

FIG. 6 is scanning electron microphotographs of an animal fat-derived extracellular matrix according to an embodiment of the present invention.

Referring to FIG. 6, in order to identify changes in cells during a solvent extraction process using supercritical fluid, a scanning electron microphotograph of adipose tissue before extraction is shown on the left, and a scanning electron microphotograph of the tissue after extraction is shown on the right.

After a solvent extraction process using supercritical fluid, all cells were removed, and the fibrous shape was identified. Therefore, it was identified that the extracellular matrix was decellularized.

EXAMPLE 2

Preparation of Animal Fat-Derived Extracellular Matrix Preservation Solution

The extracellular matrix sample obtained in Example 1 was added to deionized water at 1 wt %, mixed, and dispersed at 15° C. at a pressure of 20,000 psi using a high-pressure homogenizer.

Dispersion was repeated 5 times to prepare a dispersion. The prepared dispersion was filtered using a syringe filter having a pore size of 0.2 μm to prepare an animal fat-derived extracellular matrix preservation solution in a transparent state.

Figure 7:
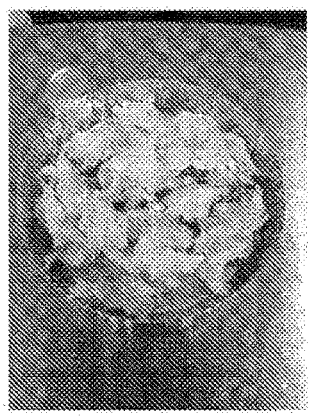
FIG. 7 is photographs of an extracellular matrix sample according to an embodiment of the present invention, a 1 wt % dispersion and an animal fat-derived extracellular matrix preservation solution prepared by filtration.
Figure 7:
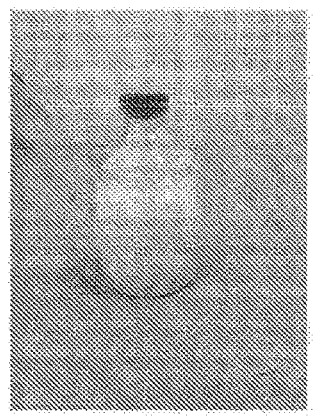
Figure 7:
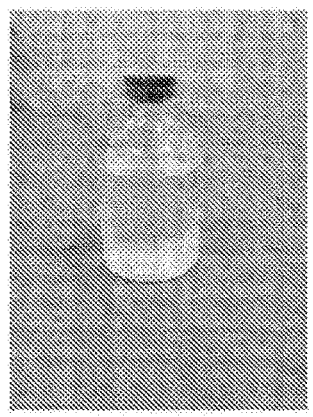

FIG. 7 is photographs of an extracellular matrix sample according to an embodiment of the present invention, a 1 wt % dispersion and an animal fat-derived extracellular matrix preservation solution prepared by filtration.

Referring to FIG. 7, it was identified that an animal fat-derived extracellular matrix preservation solution could be prepared in a transparent liquid state by dispersing the extracellular matrix sample.

EXPERIMENTAL EXAMPLE 2

Identification of Growth Factor

Enzyme-linked immunosorbent assay (hereinafter referred to as ELISA) was performed to identify whether the extracellular matrix obtained according to Example 1 contains growth factors.

A 1 wt % dispersion produced according to Example 2 was prepared and washed by adding a washing solution to each of the plate wells to be used. A standard solution (Standard) and a sample (Sample) were put into each well and reacted at room temperature for 2 hours.

The unreacted standard solution and the sample were washed with a washing solution.

Detection antibody was injected into each well, incubated for 2 hours at room temperature, and washed.

Streptavidin-HRP was injected, incubated at room temperature for 30 minutes, and then washed again.

After injection of TMB Solution, it was incubated until color development, and absorbance was measured at a wavelength of 450 nm.

Figure 8:
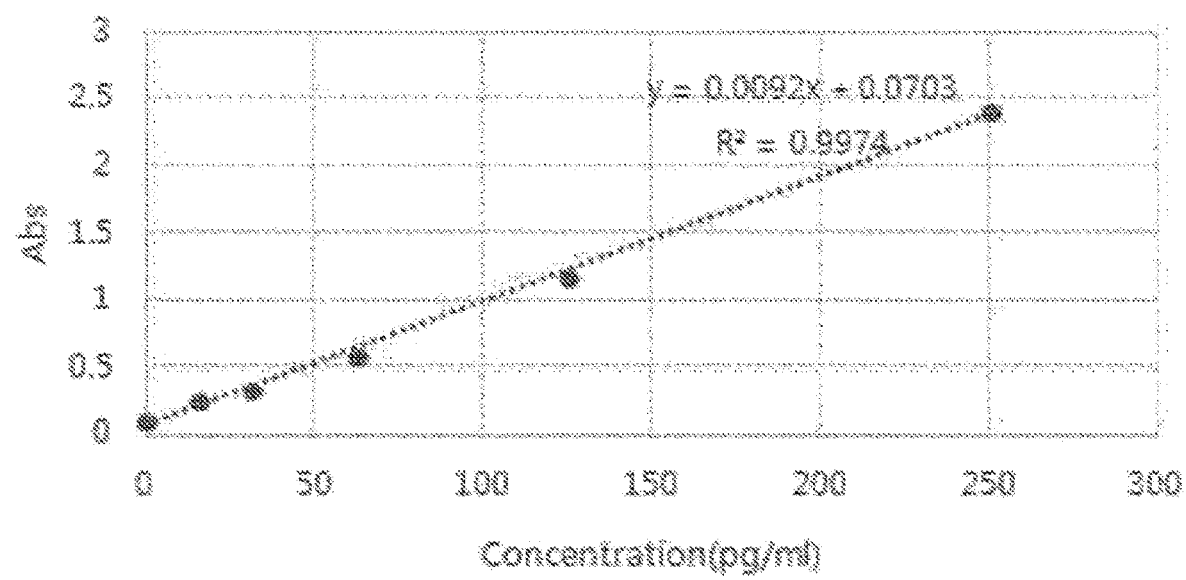
FIG. 8 is a graph showing the results of VEGF-based enzyme-linked immunosorbent assay of an animal fat-derived extracellular matrix according to an embodiment of the present invention.

FIG. 8 is a graph showing the results of VEGF-based enzyme-linked immunosorbent assay of an animal fat-derived extracellular matrix according to an embodiment of the present invention.

Figure 9:
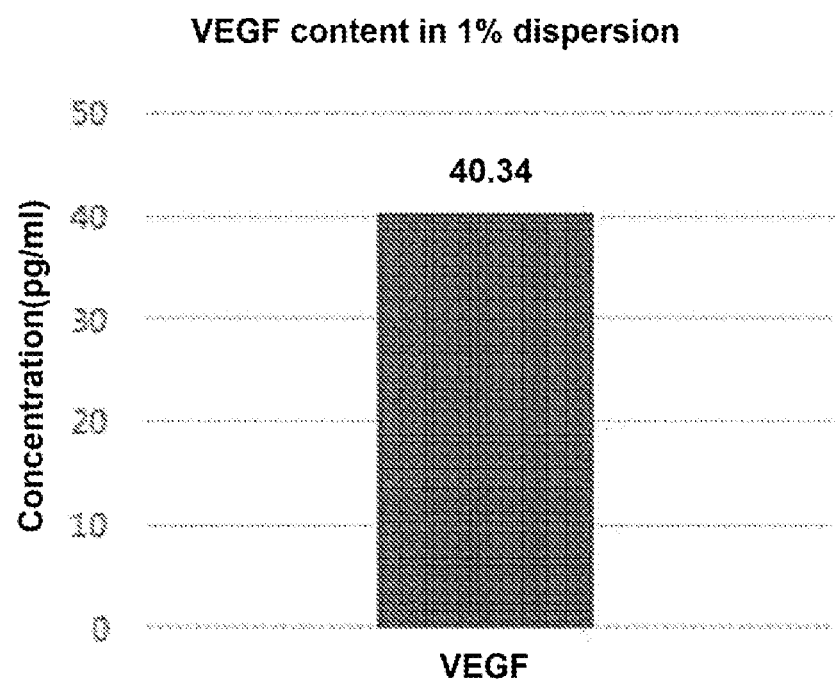
FIG. 9 is a graph showing the VEGF content in the dispersion in which an animal fat-derived extracellular matrix according to an embodiment is dispersed.

FIG. 9 is a graph showing the VEGF content in the dispersion in which an animal fat-derived extracellular matrix according to an embodiment is dispersed.

Referring to FIGS. 8 and 9, it was identified that the concentration of VEGF in the 1 wt % dispersion was 40.34 pg/ml, and the VEGF content in the extracellular matrix sample according to Example 1 was 4.03 ng/g. Therefore, it was identified that growth factors were present in the extracellular matrix sample obtained by a solvent extraction process using supercritical fluid from animal fat.

EXPERIMENTAL EXAMPLE 3

Change in DNA Content According to Filtration

The DNA content before and after filtration of the preservation solution according to Example 2 was analyzed.

Figure 10:
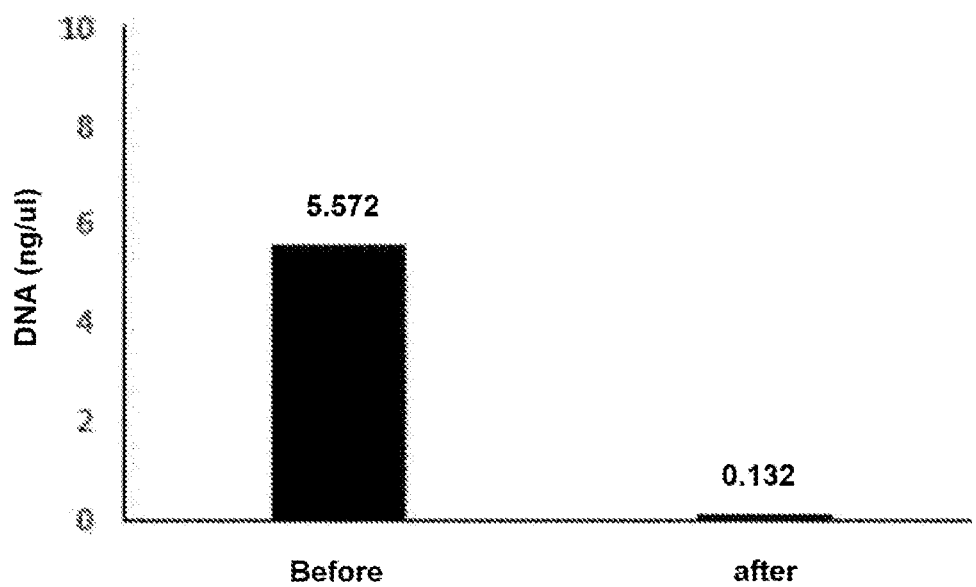
FIG. 10 is a graph showing the DNA content before and after filtration of the dispersion in which an animal fat-derived extracellular matrix according to an embodiment of the present invention is dispersed.

FIG. 10 is a graph showing the DNA content before and after filtration of the dispersion in which an animal fat-derived extracellular matrix according to an embodiment of the present invention is dispersed.

Referring to FIG. 10, it was identified that it was reduced from 5.57 ng/μl before filtration to 0.13 ng/μl, and the residual DNA may be further reduced when the extracellular matrix obtained by a solvent extraction process using supercritical fluid is dispersed and filtered.

EXPERIMENTAL EXAMPLE 4

Identification of Type and Content of Growth Factors

In order to identify that the extracellular matrix according to Example 1 contains a large amount of various growth factors, analysis was performed using a human growth factor antibody array membrane and an Abcam kit.

The sample was treated according to the protocol of the kit and diluted by 1/10 to control the concentration of protein present in the sample.

On the other hand, in order to identify the type and content of growth factors contained in the animal fat-derived extracellular matrix preservation solution according to Example 2, it was analyzed with a cytokine antibody array.

A 1 wt % dispersion (Control) and a filtration solution (Filter Solution) were prepared by 1/10 dilution, and the membrane was washed with a buffer solution (Washing buffer) and then left at room temperature for 30 minutes (Blocking).

The diluted analyte solution was applied to a membrane and incubated at 4° C. for 24 hours, and then the analyte solution was removed with an aspirator.

The remaining analyte solution was washed with a buffer solution, and biotin-conjugated anti-cytokine was injected at room temperature and incubated for 2 hours, and then the liquid was removed, and the residue was washed.

HRP-Conjugated Streptavidin was injected at room temperature and incubated for 2 hours, and then the liquid was removed, and the residue was washed.

After application of the detection buffer, images were taken with a chemiluminescence detection camera within 5 minutes and analyzed using the ImageJ program.

Figure 11:
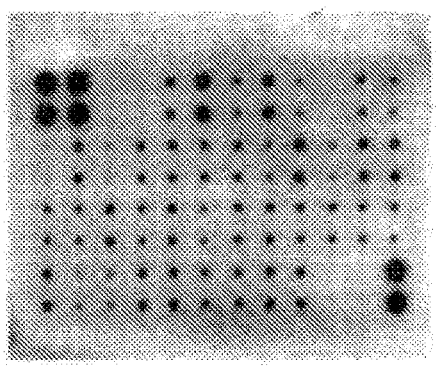
FIG. 11 is images according to the results of cytokine antibody array before and after filtration of an animal fat-derived extracellular matrix preservation solution according to an embodiment of the present invention.
Figure 11:
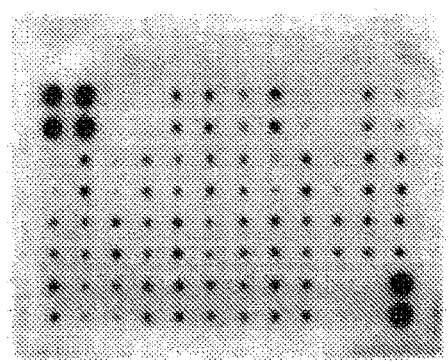

FIG. 11 is images according to the results of cytokine antibody array before and after filtration of an animal fat-derived extracellular matrix preservation solution according to an embodiment of the present invention.

The intensity of the black dots in FIG. 10 was measured using the ImageJ program.

By measuring the signal intensity of the corresponding antibody in the image measured through the cytokine array, the relative value of how much the corresponding substance is contained in the sample was identified.

It was calculated by converting the relative values of the remaining growth factors detected based on the relative values for VEGF, which is a positive control.

Figure 12:
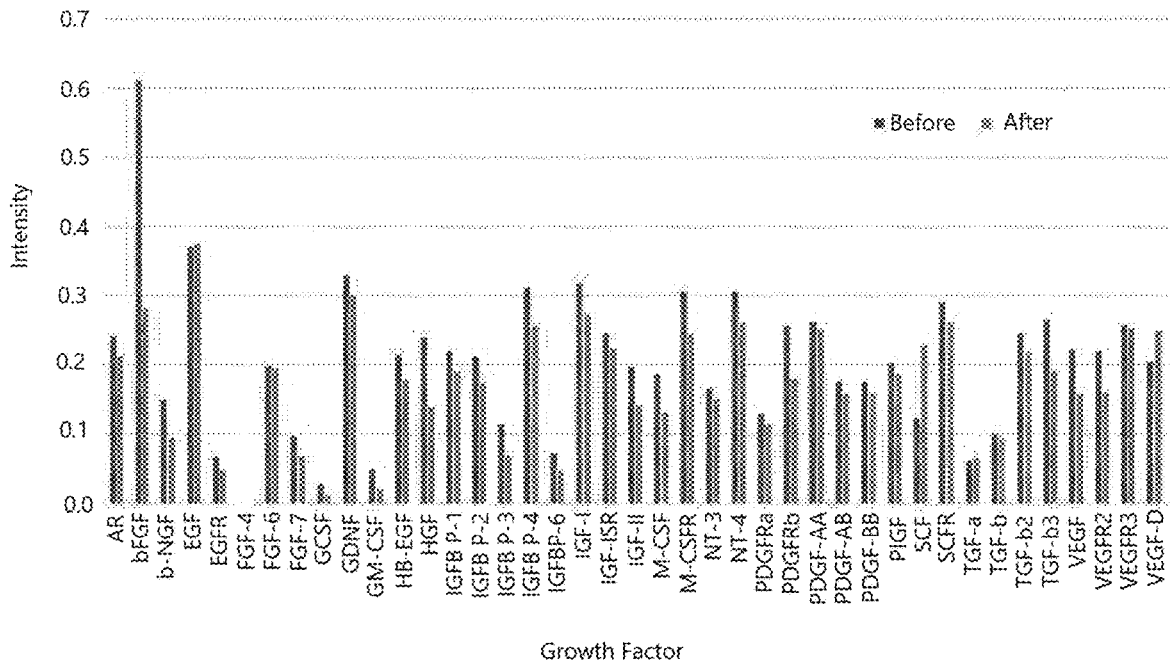
FIG. 12 shows the types and intensity of growth factors before and after filtration of an animal fat-derived extracellular matrix preservation solution according to an embodiment of the present invention.

FIG. 12 shows the types and intensity of growth factors before and after filtration of an animal fat-derived extracellular matrix preservation solution according to an embodiment of the present invention.

Referring to FIGS. 11 and 12, a total of 40 growth factors could be identified in the extracellular matrix obtained through a solvent extraction process using supercritical fluid, and it was identified that the content of the growth factors was reduced after filtration of the preservation solution containing the extracellular matrix.

Figure 13:
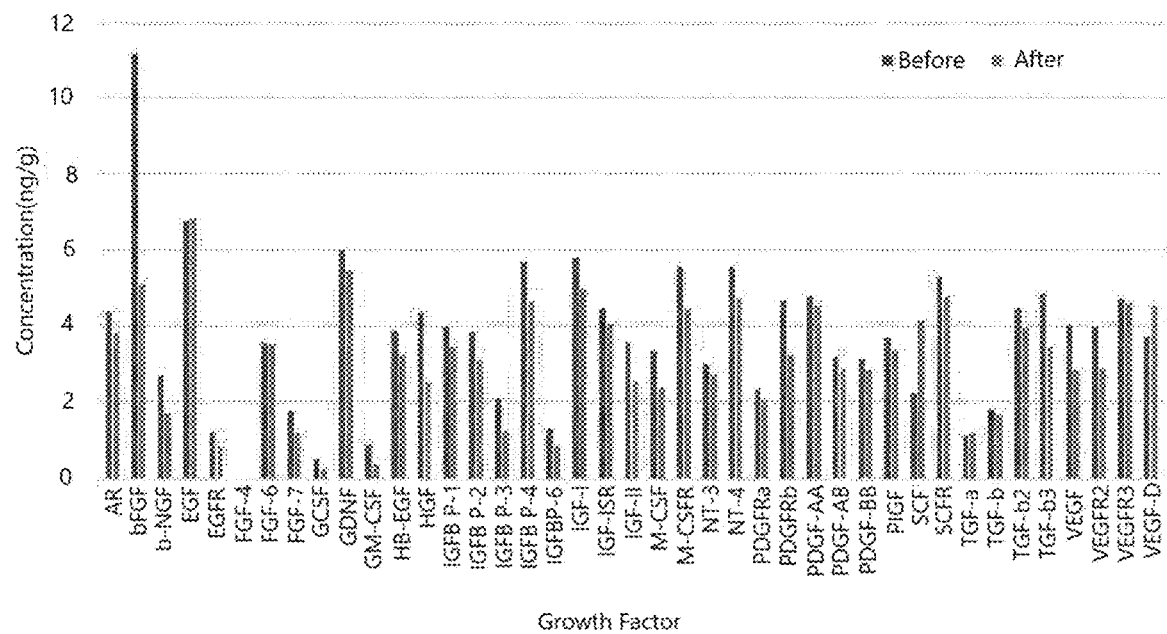
FIG. 13 shows the types and contents (ng/g) of growth factors before and after filtration of an animal fat-derived extracellular matrix preservation solution according to an embodiment of the present invention.

FIG. 13 shows the types and contents (ng/g) of growth factors before and after filtration of an animal fat-derived extracellular matrix preservation solution according to an embodiment of the present invention.

Referring to FIG. 13, it was identified that the extracellular matrix according to Example 1 contained a total of 40 growth factors out of 41 human growth factors, and that FGF-4 was removed in the solvent extraction process using supercritical fluid.

It was identified that the decellularization and fat removal effects of the solvent extraction process using supercritical fluid had an effect on the content of growth factors, and it was identified that an extracellular matrix could be obtained, in which the content and type of the growth factors were controlled according to the extraction conditions of the solvent extraction process using supercritical fluid.

On the other hand, it was identified that the animal fat-derived extracellular matrix preservation solution prepared according to Example 2 had the content of the growth factors, which was reduced from 0.21 to 6.86 ng per 1 g of the extracellular matrix according to filtration, and it was identified that the content of growth factors in the preservation solution could be controlled.

In addition, it was identified that the content of bFGF (basic fibroblast growth factor) was reduced in the range of 40 to 50% through the filtration process among growth factors, and there was a protein remaining in the 1 wt % dispersion, but bFGF contained in the protein was removed through filtration. Therefore, it was identified that the protein in the preservation solution could be removed.

This indicates that the extracellular matrix preservation solution reduces the risk of infection and contamination by removing the protein in the preservative solution, thereby increasing biosafety, sterilizing in the filtration process, and removing the remaining DNA. Therefore, it was identified that the manageability and preservation properties of the animal fat-derived extracellular matrix preservation solution could be increased.

The present inventors paid attention to the fact that a large amount of human fat is discarded according to the recent increase in liposuction. While searching for a way to utilize it, the present inventors identified that when the extraction conditions are controlled using a solvent extraction process using supercritical fluid in adipose tissue, an extracellular matrix with increased biosafety and biocompatibility may be obtained by decellularization and fat removal while maintaining the mechanical properties of the extracellular matrix.

In particular, it was identified that a large amount of growth factors remained in the extracellular matrix in the solvent extraction process using supercritical fluid, thereby controlling physiological activities of cells and rapidly inducing tissue regeneration. By identifying the characteristics of the exclusion of certain growth factors in the solvent extraction process using supercritical fluid, it was identified that it was possible to effectively extract the extracellular matrix having a different composition of growth factors from the extracellular matrix through conventional chemical and biological treatment.

So far, specific examples of the animal fat-derived extracellular matrix and the animal fat-derived extracellular matrix preservation solution according to the present invention have been described, but it is apparent that various implementation modifications are possible within the scope of the present invention.

Therefore, the scope of the present invention should not be limited to the described embodiments, but should be defined by the following claims as well as equivalents thereof.

That is, the above-described embodiments are to be understood in all respects as illustrative and not restrictive, and the scope of the present invention is indicated by the claims to be described below rather than the detailed description, and the meaning and scope of the claims, and all changes or modifications derived from the equivalent concept should be construed as being included in the scope of the present invention.

INDUSTRIAL APPLICABILITY

According to the present invention, there is provided an extracellular matrix of which the biocompatibility is greatly increased through fat removal and decellularization and which contains growth factors so as to control physiological activities of cells, and a method for preparing the same.

In addition, the extracellular matrix may be effectively obtained through a solvent extraction process using supercritical fluid.

In addition, it may be sterilized without acid, enzyme treatment and radiation treatment to increase the biosafety of the extracellular matrix, and may undergo decellularization and fat removal to increase biocompatibility.

In addition, it provides an extracellular matrix in which growth factors are preserved among the components of the extracellular matrix, and the regulation of physiological activities of cells may be expected by controlling the content of growth factors, and the regeneration of tissues may be quickly induced.

In addition, it is possible to maintain the structural properties of the extracellular matrix as it is, so that it is possible to readily prepare a tissue structure mimic that may be molded according to the shape of the transplant site.

In addition, the extracellular matrix may be effectively extracted and provided by effectively treating human-derived waste fat.

In addition, a preservation solution comprising the extracellular matrix may be preserved for a long time by preventing contamination, and has increased manageability so that usability of the extracellular matrix may be greatly increased.

The invention claimed is:

1. An animal fat-derived extracellular matrix with increased biosafety and biocompatibility, which has undergone decellularization and fat removal and includes growth factors, wherein the decellularization and fat removal and the inclusion of growth factors are carried out through a solvent extraction process using supercritical fluid, wherein the growth factor is selected from the group consisting of AR, bFGF, b-NGF, EGF, EGFR, FGF-6, FGF-7, GCSF, GDNF, GM-CSF, HB-EGF, HGF, IGFB P-1, IGFB P-2, IGFB P-3, IGFB P-4, IGFB P-6, IGF-I, IGF-ISR, IGF-II, M-CSF, M-CSFR, NT-3, NT-4, PDGFRa, PDGFRb, PDGF-AA, PDGF-AB, PDGF-BB, PlGF, SCF, SCFR, TGF-a, TGF-b, TGF-b2, TGF-b3, VEGF, VEGFR2, VEGFR3, VEGF-D, and any combination thereof, and wherein the growth factor is comprised in an amount of 0.52 to 11.19 ng per 1 g of the extracellular matrix.

2. The animal fat-derived extracellular matrix according to claim 1, wherein the animal fat is waste fat extracted through liposuction.

3. An animal fat-derived extracellular matrix preservation solution, wherein it comprises 0.1 to 5 parts by weight of an animal fat-derived extracellular matrix that has undergone decellularization and fat removal through a solvent extraction process using supercritical fluid and comprises certain growth factors; and 95 to 99.9 parts by weight of a dispersion, and is filtered.

4. The animal fat-derived extracellular matrix according to claim 3, wherein the growth factor consists of AR, bFGF, b-NGF, EGF, EGFR, FGF-6, FGF-7, GCSF, GDNF, GM-CSF, HB-EGF, HGF, IGFB P-1, IGFB P-2, IGFB P-3, IGFB P-4, IGFB P-6, IGF-I, IGF-ISR, IGF-II, M-CSF, M-CSFR, NT-3, NT-4, PDGFRa, PDGFRb, PDGF-AA, PDGF-AB, PDGF-BB, PlGF, SCF, SCFR, TGF-a, TGF-b, TGF-b2, TGF-b3, VEGF, VEGFR2, VEGFR3, and VEGF-D, and is filtered and comprised in an amount of 0.21 to 6.86 ng per 1 g of the extracellular matrix.

5. The animal fat-derived extracellular matrix preservation solution according to claim 3, wherein the growth factor has the reduced content of bFGF (basic fibroblast growth factor) in the range of 40 to 50% through the filtration.

* * * * *